US00PP32711P2

(12) United States Plant Patent
Hansen

(10) Patent No.: US PP32,711 P2
(45) Date of Patent: Dec. 29, 2020

(54) **X *MANGAVE* PLANT NAMED 'QUEEN FOR A DAY'**

(50) Latin Name: **x *Mangave* times *Agave gypsophila***
Varietal Denomination: Queen for a Day

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/873,762

(22) Filed: Jun. 26, 2020

(51) Int. Cl.
*A01H 5/12* (2018.01)
*A01H 6/12* (2018.01)

(52) U.S. Cl.
USPC ..... Plt./373
CPC ..... *A01H 6/12* (2018.05)

(58) Field of Classification Search
USPC ..... Plt./373
CPC ..... A01H 5/12; A01H 5/02; A01H 5/00
See application file for complete search history.

*Primary Examiner* — Kent L Bell

(57) ABSTRACT

A new and unique x *Mangave* plant named 'Queen for a Day' characterized by slightly-arching, slightly-wavy, lanceolate foliage with distinctly small firm spines on deeply-scalloped margins. Leaves are variegated and with strong ultraviolet light develop dark, purplish-grey margins and olive-green longitudinal centers. Plants are useful for landscaping as specimens or en masse or as container plants in the landscape or in the home.

2 Drawing Sheets

Botanical classification: x *Mangave* times *Agave gypsophila.*

Variety denomination: 'Queen for a Day'.

BACKGROUND OF THE INVENTION

The present invention relates to the new and distinct x *Mangave* x *Agave* hybrid plant, X *Mangave* 'Queen for a Day' was discovered by the inventor at a wholesale perennial nursery in Zeeland, Mich., USA in a tissue cultured batch of x *Mangave* 'Mayan Queen' U.S. Plant Pat. No. 31,312 on Apr. 13, 2019. The new plant was a whole plant mutation forming a periclinal chimera. Through trials at the same nursery the plant was originally assigned the breeder code 19-SP-MANG-836-D. The new plant has been successfully asexually propagated initially by sterile shoot-tip tissue culture at the same nursery in Zeeland, Mich. For those skilled in the art, tissue culture methods of asexual propagation systems for 'Queen for a Day' have been found to produce stable and identical plants that maintain all the unique characteristics of the original plant in successive generations.

No plants of X *Mangave* 'Queen for a Day' have been sold, under this or any name, in this country or anywhere in the world, prior to the filing of this application. No disclosure of the new plant been made prior to the filing of this application with the exception of that which was disclosed within one year of the filing of this application, and was either derived directly or indirectly from the inventor.

BRIEF SUMMARY OF THE INVENTION

X *Mangave* 'Queen for a Day' differs from its parent mutation as well as all other *Manfreda, Agave*, and X *Mangave* known to the applicant. Compared with 'Mayan Queen' the new plant has foliage with a longitudinal olive-green center and solid, dark, purplish-grey margins. Other similar cultivars known to the inventor are x *Mangave* 'Red Wing' U.S. Plant Pat. No. 31,459, x *Mangave* 'Silver Fox' U.S. Plant Pat. No. 29,642, x *Mangave* 'Purple People Eater' U.S. Plant Pat. No. 29,949, x *Mangave* 'Painted Desert' U.S. Plant Pat. No. 31,630 x *Mangave* 'Lavender Lady' U.S. Plant Pat. No. 29,194 and x *Mangave* 'Shadow Waltz' U.S. Plant Pat. No. 31,601. 'Red Wing' has a more compact habit and the foliage is more reddish spotted without the longitudinal olive-green center. 'Purple People Eater' has shorter, less arching foliage with purple markings that are more spotted and less dense and without the longitudinal olive-green center, smaller marginal and apical spines and a more compact habit. 'Silver Fox' is more compact and has smaller foliage with more intense glaucous surfaces and purple spots without the longitudinal olive-green center. 'Mission to Mars' has a larger habit with broader and longer foliage that is less glaucous and has intense reddish markings and lacks the olive-green leaf center. 'Painted Desert' has narrower foliage with smaller marginal teeth and the purplish color is more spotted with reddish coloration in the center when grown in high intensity ultraviolet light and more chartreuse when grown in low intensity ultraviolet light. 'Lavender Lady' has shorter more ovate foliage having more uniform concentration of purplish spotting and without the longitudinal olive-green center and no marginal teeth on the foliage and the habit more upright with no arching of the foliage. 'Shadow Waltz' has narrower foliage with smaller marginal teeth and a chartreuse center with moderate green margins but no intense purple spotting or marking.

The new plant, 'Queen for a Day', is unique from all of the above cultivars and all *Agave*, x *Mangave*, and *Manfreda* known to the inventor by the following combined traits:

1. Slightly-arching, slightly-wavy, lanceolate foliage with small, firm, apical spines and deeply-scalloped leaf margins;
2. Dark, purplish-grey foliage margins with olive-green, longitudinal centers with heavy glaucous covering;

3. Leaves have sharp, firm, apical spines and marginal teeth;
4. Moderate growth rate.

BRIEF DESCRIPTION OF THE DRAWINGS

The photographs of x *Mangave* 'Queen for a Day'; demonstrate the overall appearance of the new plant including the unique traits of a fourteen-month-old plant grown in a full-sun outdoor trial garden in Zeeland, Mich. The colors are as accurate as reasonably possible with color reproductions. Ambient light spectrum, temperature, source and direction may cause the appearance of minor variation in color.

DETAILED BOTANICAL DESCRIPTION

Figure 1:
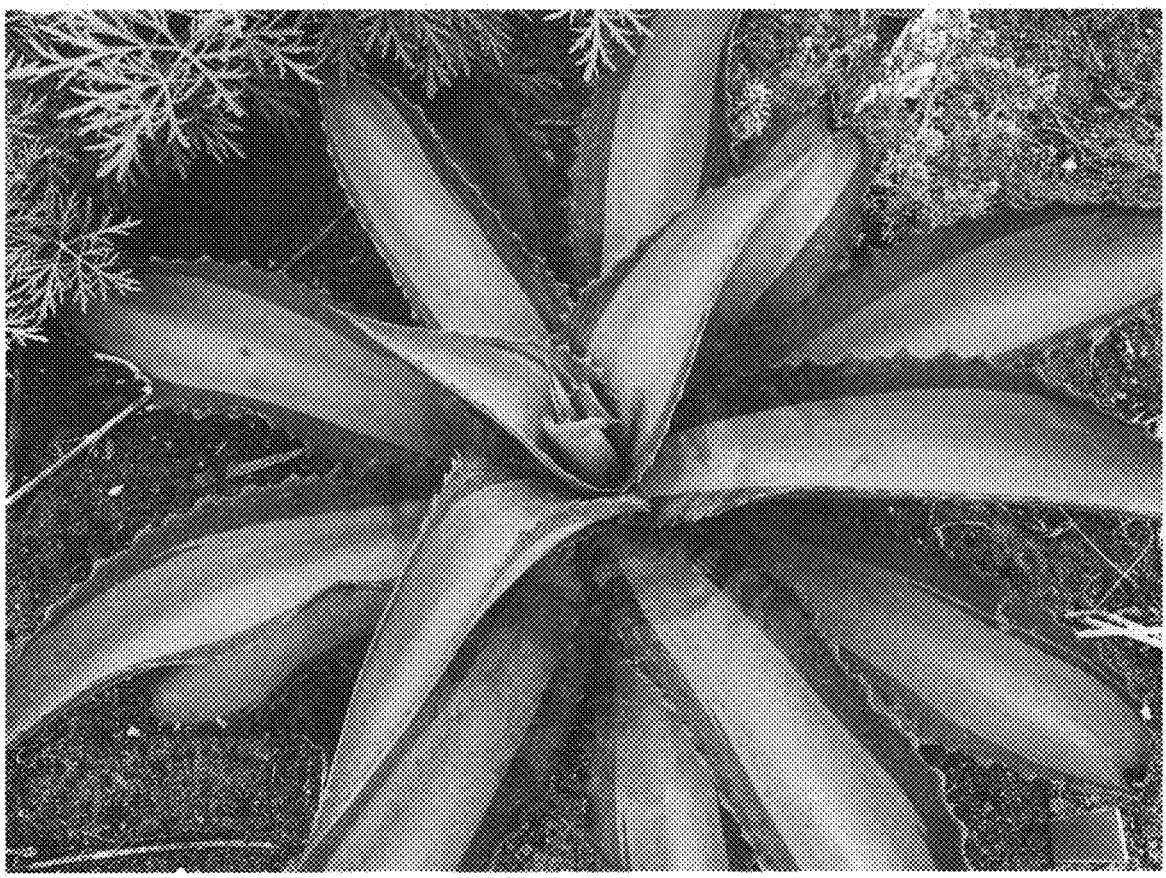
FIG. 1 shows the new plant foliage and habit from above.
Figure 2:
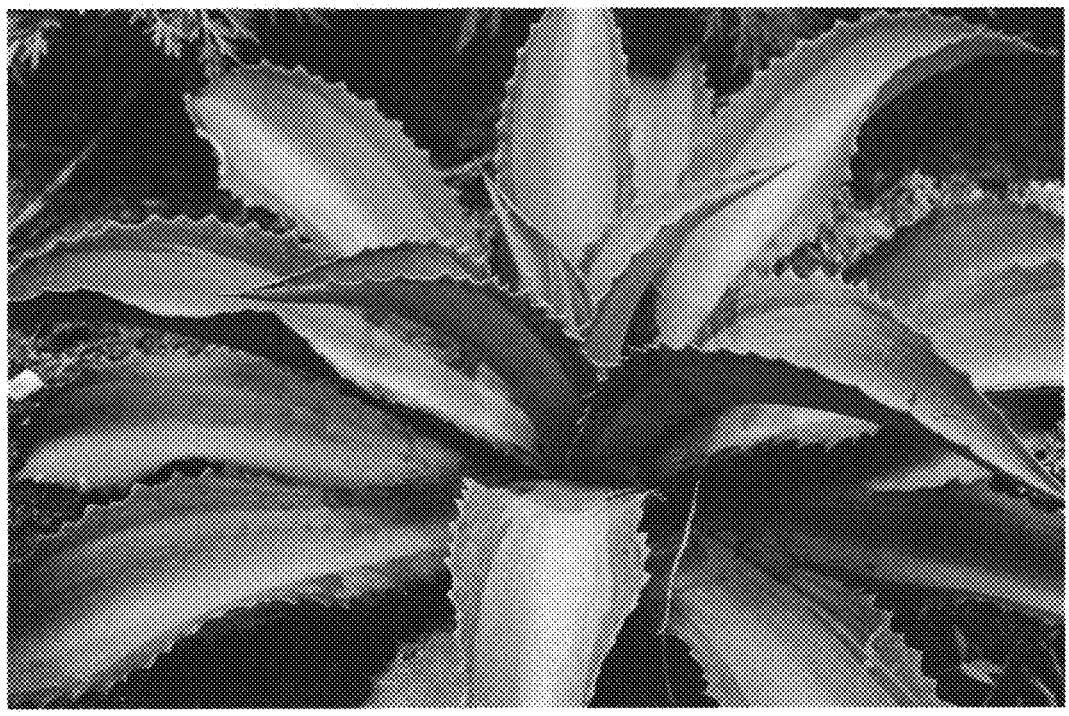
FIG. 2 shows the new plant foliage and habit from a side view.
Figure 3:
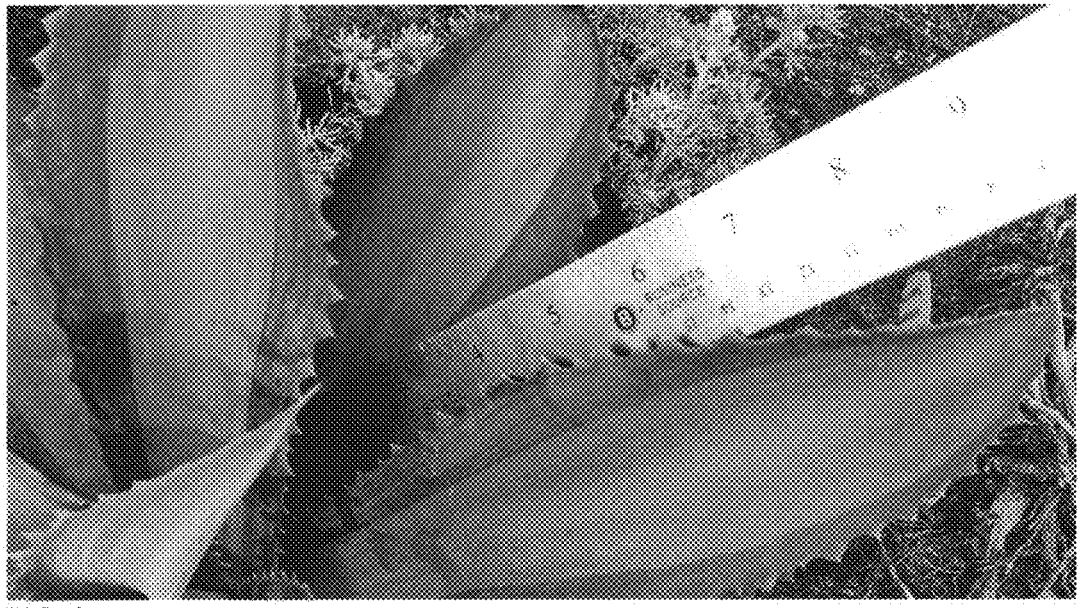
FIG. 3 shows a close-up of the foliage and marginal teeth from above.

The following descriptions and color references are based on The 2015 edition of The Royal Horticultural Society Colour Chart except where common dictionary terms are used. The new plant, X *Mangave* 'Queen for a Day', has not been observed under all possible environments. The phenotype may vary slightly with different environmental conditions, such as temperature, light, fertility, moisture and maturity levels, but without any change in the genotype. The following observations and size descriptions are of a one-year-old plant moved from a commercial wholesale greenhouse to a full-sun trial garden in Zeeland, Mich. with supplemental water and fertilizer as needed.

Parentage: X *Mangave* 'Mayan Queen' whole plant mutation;

Propagation: Sterile shoot-tip tissue culture;

Time to initiate roots from tissue culture: About 21 days;

Growth rate: Moderate;

Crop time: About 12 to 16 weeks to finish in a 3.8 liter container from a 35 mm tissue culture growing at about 21° C.;

Rooting habit: Fleshy, lightly branching, with roots up to 20 cm long;

Root color: Nearest RHS 158D;

Plant shape and habit: Succulent, herbaceous, freeze-tender perennial with basal rosettes of about 25 leaves radially emerging and outwardly and slightly arching from central stem extending below the base of the plant when grown in containers, producing a radially-symmetrical, slightly outwardly mound;

Plant size: Foliage height about 18.0 cm tall from soil line to the top of the leaves and about 48.0 cm wide at the widest point near soil line;

Foliage description: Lanceolate; simple; margins scalloped with small firm teeth; apex spinose; base truncate, sessile, clasping; flat; bi-laterally symmetrical; slightly involute to slightly conduplicate;

Leaf size: To about 26.0 cm long, about 7.0 cm wide at base and 5.0 mm thick, average about 24.0 cm long, 6.5 cm wide and 4.5 mm thick; marginal teeth about 1.0 mm long on scalloped indentations about 5.0 mm deep and about 7.0 mm apart; adaxial margin to about 18.0 mm wide and center to about 36.0 mm wide; abaxial margin to about 4.0 mm wide and center to about 56.0 mm wide;

Foliage fragrance: None observed;

Leaf blade color:

*Adaxial* (*young*).—Center nearest RHS 138B, and margin between RHS N187A and RHS 187A with intense ultraviolet light.

*Abaxial* (*young*).—Center a blend between RHS N138A, RHS 189A and RHS 189B, and margin between RHS N187A and RHS N187B with intense ultraviolet light.

*Adaxial* (*mature*).—Center between RHS 137A and RHS 137B, and margin nearest RHS N187A.

*Abaxial* (*mature*).—Center between RHS 138A and RHS 138B, and margin mixture of RHS 138B and RHS N187A.

*Teeth*.—Young adaxial and abaxial bases nearest RHS 185C with 1.0 mm long apices nearest RHS 160D; mature adaxial base nearest RHS N187A, abaxial base mottled with RHS 138B and transitioning to solid RHS N187A distally; mature apices nearest RHS 200A.

Apical spine or mucro: Sharp and firm; average about 7.0 mm long and about 1.0 mm wide at base;

Apical spine or mucro color: Between RHS 179B and RHS 182A on young expanding leaves and maturing to nearest RHS 200B;

Petiole: Sessile;

Veins: Parallel; not distinct abaxial or adaxial;

Stem: Terete; covered with leaves; about 5.0 cm across and extending to about 4.0 cm above soil; without branching; attitude upwards, erect;

Flowers have not yet been observed.

Fruit and seed have not yet been observed.

Disease resistance: X *Mangave* 'Queen for a Day' has not been observed to be resistant to diseases beyond that which is normal for X *Mangave, Agave* or *Manfreda*. The plant is xeromorphic and survives well with minimal water once established. The new plant is hardy at least from USDA zone 9a to 11. Full extent of winter hardiness has not been tested.

It is claimed:

1. A new and distinct cultivar of ornamental x *Mangave* plant named 'Queen for a Day' as herein described and illustrated, suitable for the garden or as a potted plant in the garden or home.

* * * * *